United States Patent
Kraus et al.

(10) Patent No.: US 8,702,581 B2
(45) Date of Patent: Apr. 22, 2014

(54) APPARATUS FOR STIMULATING A HEALING PROCESS

(75) Inventors: Werner Kraus, Munich (DE); Stephanie Kraus-Geiges, Munich (DE); Heribert Stephan, Munich (DE)

(73) Assignee: Neue Magnetodyn GmbH, Munich (DE)

( * ) Notice: Subject to any disclaimer, the term of this patent is extended or adjusted under 35 U.S.C. 154(b) by 367 days.

(21) Appl. No.: 12/990,259

(22) PCT Filed: Mar. 19, 2009

(86) PCT No.: PCT/EP2009/002047
§ 371 (c)(1),
(2), (4) Date: Mar. 23, 2011

(87) PCT Pub. No.: WO2009/132732
PCT Pub. Date: Nov. 5, 2009

(65) Prior Publication Data
US 2011/0213195 A1    Sep. 1, 2011

(30) Foreign Application Priority Data
Apr. 30, 2008 (DE) .......................... 10 2008 021 575

(51) Int. Cl.
*A61N 1/00*     (2006.01)
(52) U.S. Cl.
USPC .................................. 600/14; 600/13; 600/15
(58) Field of Classification Search
USPC ....................................................... 600/13, 14
See application file for complete search history.

(56) References Cited

U.S. PATENT DOCUMENTS

| | | | | |
|---|---|---|---|---|
| 4,082,097 A | * | 4/1978 | Mann et al. | 607/33 |
| 4,266,532 A | * | 5/1981 | Ryaby et al. | 600/14 |
| 4,501,265 A | | 2/1985 | Pescatore | |
| 4,817,612 A | * | 4/1989 | Akins et al. | 600/422 |
| 5,755,748 A | * | 5/1998 | Borza | 607/61 |
| 5,820,548 A | | 10/1998 | Sieben et al. | |
| 6,117,292 A | * | 9/2000 | Ahmad | 204/416 |
| 2008/0154265 A1 | | 6/2008 | Duda et al. | |
| 2009/0281419 A1 | | 11/2009 | Troesken et al. | |
| 2010/0036467 A1 | | 2/2010 | Kraus et al. | |

FOREIGN PATENT DOCUMENTS

| | | |
|---|---|---|
| DE | 33 43 182 A1 | 7/1984 |
| DE | 196 01 487 A1 | 7/1997 |
| DE | 10 2006 029 122 A1 | 12/2007 |
| EP | 0 500 983 A1 | 9/1992 |

(Continued)

OTHER PUBLICATIONS

International Search Report dated Aug. 3, 2009 with English translation (six (6) pages).

*Primary Examiner* — Jacqueline Cheng
*Assistant Examiner* — Kaylee Wilson
(74) *Attorney, Agent, or Firm* — Crowell & Moring LLP

(57) ABSTRACT

The invention relates to an apparatus for stimulating a healing process comprising a coil arrangement which is coupled to a functional power generator in order to generate an electromagnetic field in an affected body region, a control unit for influencing a voltage curve generated by the functional power generator in accordance with signals transmitted to an input interface of the control unit, a sensor array for sensing a characteristic of the affected body region, transmission device which is coupled to the sensor array in order to transmit a signal characteristic of the detected characteristic of the affected body zone to the control unit.

14 Claims, 8 Drawing Sheets

(56) References Cited

FOREIGN PATENT DOCUMENTS

| EP | 2 074 958 A2 | 7/2009 |
| WO | WO 2005/074821 A2 | 8/2005 |
| WO | WO 2007/124731 A2 | 11/2007 |
| WO | WO 2008/035089 A1 | 3/2008 |

* cited by examiner

APPARATUS FOR STIMULATING A HEALING PROCESS

BACKGROUND AND SUMMARY OF THE INVENTION

The invention relates to an apparatus for stimulating a healing process.

The use of electromagnetic fields for the treatment of large wounds of the soft tissue, the musculature and the skin can often considerably accelerate the healing process. In particular, there are diseases which are resistant to antibiotic therapy, which may, for example, be caused by MRSA (Methicillin-resistant *Staphylococcus aureus*) and other germs such as enterococci or pseudomonads. This therapy resistance may be overcome by the application of electromagnetic fields.

Electromagnetic therapies have, for example, been successful in the treatment of badly healing bone fractures, as well as of associated, mostly bacterially induced secondary diseases. The so-called "venous ulcer" (ulcus cruris) can also be successfully treated with electromagnetic fields. Furthermore, dermatological applications, such as the treatment of large chronic wounds in the skin like ulcera cruris or burns, play an important role in connection with the electromagnetic fields therapy. For example, higher-degree burns may render skin transplants necessary; the transplants can be prepared by externally applied magnetic fields and after transplantation, healing can be supported by these fields.

The applied alternating electromagnetic fields have, for example, a magnetic field intensity of 1 to 5 mT and a sinusoidal waveform having a frequency of 1 to 20 Hz. The generation of the fields is effected using magnetic coils excited by a corresponding alternating current. Different coil arrangements may be utilized, for example, solenoid coils or Helmholtz coils, depending on the application and the desired direction of the magnetic field.

In numerous studies of fundamental in vivo and in vitro research, a specific correlation of growth and differentiation of human connective tissue and bone cells, namely fibroblasts and osteoblasts, and the influencing parameters of the electric and of the magnetic field became apparent. Proliferating cells and tissue growth were predominantly observed in the area of the electric field gradients, i.e. in the vicinity of electrodes in galvanic contact with tissue. In contrast, the number of differentiating cells grew with a corresponding intensification of their metabolism and the controlled synthesis of structural proteins—at decreasing mitosis rates—in the extended volume of the tissue pervaded by the magnetic field.

The object of the present invention is to develop a stimulation apparatus which works on the basis of electromagnetic alternating fields, is capable of supporting the healing of an affected body region and can be adapted to the various healing phases.

The invention consists of an apparatus for stimulating a healing process comprising a coil arrangement coupled to a functional power generator for generating an electromagnetic field in an affected body region, a control unit for influencing a voltage curve generated by the functional power generator dependent on signals transmitted to an input interface of the control unit, a sensor array for detecting a characteristic of the affected body region and a transmission device coupled to the sensor array for transmitting signals characteristic of the detected characteristic of the affected body region to the control unit. The stimulation apparatus can, therefore, modulate the electromagnetic field in the affected body region dependent upon the characteristics detected the sensor array. If the characteristics of the affected body region detected by the sensor array change during the healing process, the modulation capability of the apparatus ensures that the healing process can be optimally adapted at any time, in order to ultimately result in an acceleration of the healing process as well as increased therapeutic success.

In this connection, it is particularly advantageous that the sensor array comprises a pH-sensor. The pH-value present in the area of affected body regions is an indication of the biochemical quality of the tissue. For example, in the area of a large soft tissue injury, such as second or third degree burns or pathologically changed ulcerative wounds, the effectiveness of therapeutic measures such as bandages or skin transplantations including chemical anti-bioses in case of bacterial infections can be estimated by the change in the wound's pH-value, and a corresponding change of the treatment methods can be implemented. The requirements of a therapeutically optimal regulation of the wound environment are met by a pH-value controlled and modified induction of the damaged soft tissue by extremely low-frequency, non-thermal magnetic and electric fields having temporally changeable waveforms (signal forms). Other sensors may also be used instead of or in addition to pH-sensors, for example, temperature sensors, conductivity sensors and/or sensors for detecting the presence and/or the concentration of certain chemical substances.

According to one embodiment of the present invention, it is contemplated that the transmission device comprises at least one electric line directly connected to the input interface of the control unit. Thus, the electric signals supplied by the sensor array can be transmitted to the control unit of the functional power generator without any particular technical complexity.

However, it is also feasible that the transmission device comprises at least one transmitter for a wireless communication with a receiver allocated to the input interface of the control unit. Such a transmitter may have various designs. However, it is important that it translates the measured values detected by the sensor array in order for corresponding signals to be transmitted to the receiver of the control unit. One option for the information transfer from the transmitter to the receiver in the control unit is the active generation of transmission signals dependent upon the measured values of the sensor array.

It may, however, also be contemplated that the transmission device comprises at least one RFID transponder, the information content of which is detectable by a reading device associated with the input interface of the control unit. An RFID transponder is a device which can only "transmit" information through interaction with a reading device. For this purpose, the RFID transponder ultimately receives an electromagnetic high frequency field generated by the reading device in order to then change it depending upon information stored in the RFID transponder. The change is then detected by the reading device. Due to this very limited functionality of an RFID transponder, it is inexpensive and space-saving in comparison to conventional active transmitters.

The information transfer from the RFID transponder to the reading device can take place, as the readable information content of the RFID transponder can be changeable dependent on signals supplied by the sensor arrangement. In the simplest case, the sensing device applies different voltages to the memory of the RFID transponder, wherein said voltages depending on the voltage detected by the sensing device, or is the detected voltage itself; in the latter case, the sensing device and the transmission device are to be referred to as integrated or identical. Different voltages can now cause the content of the memory of the RFID transponder to change so that ultimately the identification transmitted to the reading device by the RFID transponder is also changed. The use of writable RFID transponders is required to enable a change of the content of the memory of the RFID transponder.

Alternatively or additionally, however, it is also possible to provide a plurality of RFID transponders which can be activated or deactivated dependent on signals supplied by the sensor array. In this case, non-writable transponders are sufficient. One or more threshold circuits integrated in the sensing device and the RFID transponders ensure that different RFID transponders are active or inactive dependent on the supplied voltage. Thus, the reading device can also receive different identifications dependent on the voltage and, therefore, ensure that the functional power generator generates a voltage curve adjusted to the detected characteristics of the affected body region.

Usefully it is contemplated that the sensor array comprises an ion-sensitive field effect transistor. These semiconductor components are capable of detecting the pH-value, and extremely small version of these components can be produced and purchased for use in connection with numerous diseases.

The invention is further enhanced in a particularly advantageous manner in that the coil arrangement comprises a coil comprising a coil winding having an intersection point which defines two surfaces by a figure eight shaped form, the surfaces being aligned relative to each other so that the magnetic fields generated by a current flow in the coil arrangement and pervading the surfaces are substantially rectified. In this manner, the effect of two separate induction coils whose magnetic fields have the same direction in which the injured body region is located can also be obtained with a single coil. This renders the application comfortable, particularly owing to the reduced mechanistic complexity.

It is usefully contemplated that the coil arrangement is flexible so that the surfaces can be positioned on the opposing sides of the body region which is to be exposed to the magnetic field. Due to its flexible winding which may result from the elasticity of the used material, it is possible to reshape the coils in order to obtain a figure eight or infinity symbol. The "loops" of the coil resulting from said reshaping may, for example, be positioned at both sides of an extremity. Depending on the application, they may have the same or different sizes. The coil arrangement can also be used very versatilely thanks to its flexibility. In connection with the design of the coil arrangement, it may be contemplated that fasteners for establishing and maintaining the alignment of the surfaces in respect to each other are provided in two positions of the coil arrangement facing away from the intersection point. The fasteners may, for example, be belts, snaps, hook-and-loop fasteners, buckles or the like. In a particularly advantageous manner, it may be contemplated that the intersection point of the coil arrangement is fixable by means of a coupling device. Such a coupling device may, for example, be realised by an elastic strap having a hook-and-loop fastener or a belt buckle. It is particularly advantageous that the position of the intersection point and, thus, that the dimensions of the surfaces are variable. As the surface ratio of the coil loops can be adjusted in this manner, the magnetic induction flux density, which is defined as the quotient of the magnetic flux and the observed surface, is also adjustable. The ratio of the induction flux densities is the reciprocal value of the ratio of the respective surfaces. The surface ratio of the two loops may be selected according to the therapeutic requirements by changing the fixation of the intersection point by a variable positioning of the coupling device. For example, a high magnetic induction flux density may be obtained in a target area of the body by positioning a small-surface coil loop in its proximity, while with regards to the other, large-surface coil surface, its parallel arrangement relative to the smaller surface must primarily be regarded in order to provide the Helmholtz coil effect. With such a coil arrangement, it is accomplished that the magnetic field of the two loops of the coil arrangement opposite each other is rectified by the spatial reversal of the current direction in one of the two loops similar to the arrangement of two separate coils according to Helmholtz, whereby a particularly good and flexible manageability is achieved. Convenient handling during the adjustment of the geometric shape of the coil arrangement to the position of the respective bones or soft tissue lesion is possible. For example, the loop surfaces can be adjusted to treatment areas such as foot, knee, lower leg, thigh, pelvis, spine, hand, lower arm, upper arm, jaw and skull regions by varying the loop shapes and sizes. The loop shapes and sizes can also be varied in respect to the intensity of the magnetic field. Another feature of the coil arrangement according to the invention is an increase of the flux density in the area proximate to the intersection point so that a relatively strong magnetic field can be concentrated on a small body surface. Thus, highly localised diseases such as abscesses and infections can be treated effectively. According to a particularly preferred embodiment of the invention, the coil arrangement is further developed so that it has plastic qualities. Due to the flexibility of the coil, it can be adjusted to the body region to be treated, whereas the plasticity keeps the coil arrangement in the reshaped position. The plastic qualities can thusly act as support for other fixation means such as buckles or clamps or, alternatively, alone provide for the stability of the coil in the desired shape. Usefully, it is contemplated that the plastic qualities are provided by at least one plastic material component surrounded by and/or embedded in at least one non-plastic material component. The coil can thus be manufactured from a flexible material irrespective of if it has plastic qualities. The plastic qualities are then provided to the coil by a plastic material component so that the overall coil remains in the position produced by reshaping. This may in particular be realised by forming the at least one plastic material component of at least one strand of a plastic material extending largely parallel to the coil winding. One or more such strands extend entirely or partly parallel to the windings of the coil. It is particularly easy to produce a coil designed in this manner.

The invention is, in a particularly advantageous manner, further developed in that the functional power generator is adapted to generate virtually purely harmonic voltage curves having a fist harmonic wave component or abnormally harmonic voltage curves having a second harmonic wave component which is larger than the first harmonic wave component dependent on signals transmitted to the input interface of the control unit. The harmonic wave components of the electromagnetic field in the affected body region can be varied by changing the voltage curve generated by the functional power generator. In particular, the frequency of the low-frequency magnetic field can be maintained, while the electric fields which depend on the temporal differential of the magnetic field can be varied up to high frequencies. In this manner, the affected body region can be exposed to virtually invariable low-frequency alternating magnetic fields which promote the differentiation of the cells, while high-frequency components are generated if appropriate per the values, and in particular, the pH-values detected by the sensor array.

In concrete terms for wound healing on the human body, it is particularly preferred that the functional power generator is capable of generating a virtually purely harmonic voltage curve having a frequency of 1 to 30 Hz at a pH-value detected by the sensor array of less than 7 and to generate an abnormally harmonic voltage curve having a fundamental frequency of 1 to 30 Hz and physiologically effective harmonics having five to fifty times the fundamental frequency at a pH-value detected by the sensor array of more than 7. While low pH-values of less than 7 occur at the beginning and at the end of the treatment, pH-values above 7 are observed in the main phase of the healing process, namely in the growth phase of the connective tissue. During this growth phase, it is particularly advantageous to expose the wound area to high electric field intensity. In contrast, this is not required at the beginning of the healing process and, in particular, contraindicated at the end of the treatment when the pH-value returns to values below 7, so that the electric stimulation of tissue growth can be reduced to the benefit of the magnetically stimulated differentiation of cells and tissue structures. The term "physiologically effective harmonics" means in the present context that they have an intensity which still influences the healing process with a verifiable effect. For example, the intensity of such harmonics which are still physiologically effective may be in a range of 5 to 15% of the basic waveform.

According to another preferred embodiment of the invention, it is contemplated that electrodes coupled to a repeating coil are provided to be positioned in or at the affected body region. Such electrodes are also referred to as wound electrodes and may be used especially in the case of therapy-resistant ailments. In addition to the already existing field penetration of the affected body region, a repeating coil is also excited by the external magnetic field so that a targeted and amplified application of an alternating electric field to the wound area is possible due to the coupling of the electrodes to the repeating coil.

The present invention relates to an apparatus for stimulating a healing process. The invention could, however, also be formulated as a method in which the following process steps are of significant relevance: generation of an electromagnetic field in an affected body region; detecting a feature of the affected body region; transmitting signals characteristic of the detected feature of the affected body region to a control unit of a functional power generator; influencing a voltage curve generated by the functional power generator dependent on the transmitted signals. Particularly advantageous embodiments of this method are characterised in that a pH-value is measured as a characteristic of the affected body region, and/or the transfer of information to the control unit is effected using at least one RFID transponder. Furthermore, the method is, in a particularly useful manner, embodied so that a virtually purely harmonic voltage curve having a frequency of 1 to 30 Hz is generated at a detected pH-value of less than 7, and an abnormally harmonic voltage curve having a fundamental frequency of 1 to 30 Hz and physiologically effective harmonics having five to fifty times the fundamental frequency is generated at a pH-value of more than 7.

BRIEF DESCRIPTION OF THE DRAWINGS

The invention will now be discussed by way of example with the aid of particularly preferred embodiments with reference to the accompanying drawings in which.

DETAILED DESCRIPTION OF THE DRAWINGS

Figure 1:
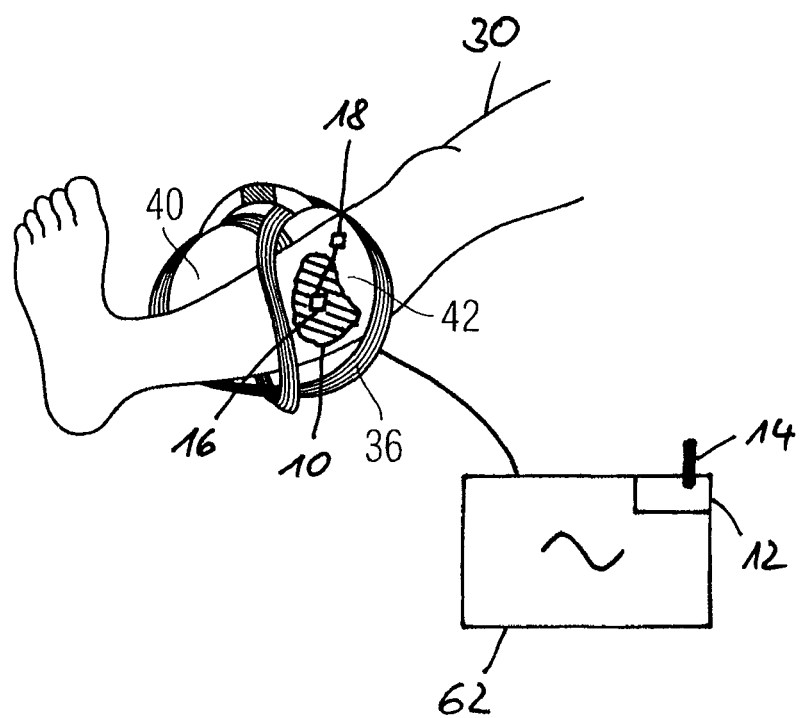
FIG. 1 shows an apparatus according to the invention during its application.

In the following description of the drawings identical reference numerals designate the same or comparable components.

FIG. 1 shows an apparatus according to the invention during its application. A leg 30 with a wound area 10 on the lower leg can be seen. The inducing electromagnetic field is generated in a flexible magnetic coil 36 by a functional power generator 62. For a better illustration, the flexible coil 36 was illustrated at a distance to the affected body region. In practice, however, the magnetic coil 36 is preferably formed directly to the injured body region in the treatment of a large wound 10 so that its winding immediately surrounds the wound area 10. The vectors of the coil field permeate the wound surface 10 at approximately a right angle. At least one pH-sensor 16 in the form of an ion-sensitive field effect transistor for measuring the pH-value of the wound is fixed in the desired position (centre or edge of the wound) in direct contact to the damaged tissue by means of a bandage (not shown) or an adhesive plaster (not shown). The measured pH-value is transmitted to the input interface 14 of the control unit 12 of the functional power generator of the magnetic coil via cable or by transfer via one or more RFID transponders 18 electrically connected to the sensor 16 so that the pH-value can form the basis for the modulation of the voltage curve exciting the coil 36 and thus the electromagnetic field pervading the wound 10. To ensure a smooth transfer of the high-frequency electromagnetic signals between the RFID transponder 18 and the input interface of the control unit 12 formed as a reading device 14, it may be required to interrupt the generation of the electromagnetic fields in the magnetic coil 36 for a short period of time for the purpose of communication.

Figure 2:
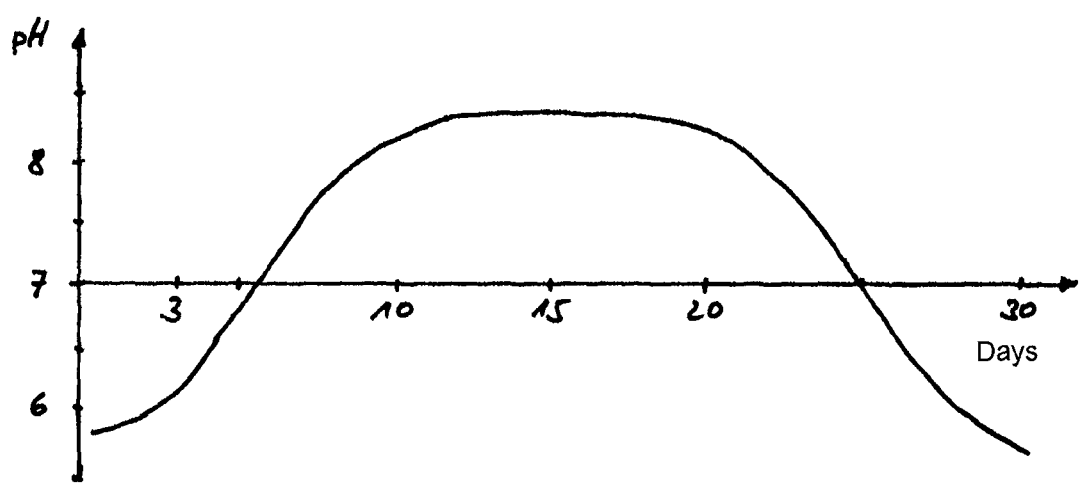
FIG. 2 shows a typical progression of the pH-value in a large wound healing by second intention over 30 days.

FIG. 2 shows a typical progression of the pH-value in a large wound healing by second intention over 30 days. At the beginning of the treatment with a pH-value of less than 7, surgical debridgement is often carried out in order to free the wound of necrotic tissue and promote the formation of blood vessels (capillaries). The pH-value rises to the neutral value of 7. On the third to fifth day thereafter, the synthesis of the collagenous connective tissue by fibroblasts forming in the direct vicinity of the blood vessels begins. At an increasing pH-value (pH>7 to 8), autonomous granulation tissue also develops which forms the biological and biomechanical basis for a possible skin transplant. Re-epithelialisation, i.e., the final phase of the wound healing, exhibits decreasing pH-values from below 7 down to a pH-value of 4, which characterise the protective acid coat of the uninjured skin. A major factor influencing the pH-value is the oxygen respiration of the cell. The absorption of—paramagnetic—$O_2$ molecules and their phosphorylation to ATP—the energy storage of the cell—at the internal membranes (mitochondria) is predominantly induced by the magnetic field which, in contrast to the electric field, permeates the cell unchanged. By reductive and oxidative reactions for charge separation at the beginning of the respiration chain, two protons (2H$^+$) are discharged per $O_2$ molecule. The decreasing extracellular pH-value forms an effective, neuro-vegetative signal which causes a regulative increase of the blood flow in the wound area.

Figure 3:
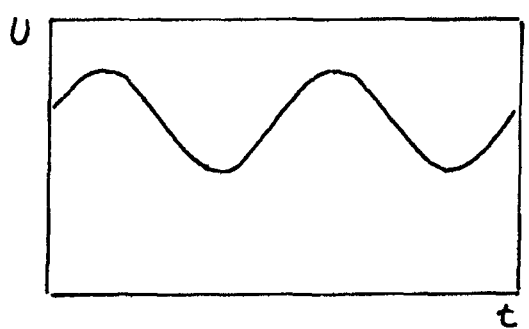
FIG. 3 shows a purely harmonic voltage curve.
Figure 4:
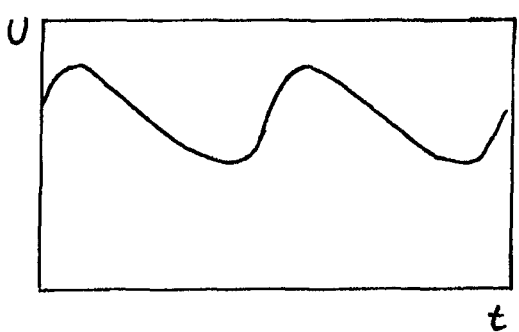
FIG. 4 shows an abnormal harmonic voltage curve.

FIGS. 3 and 4 show signal curves which can be generated by the apparatus according to the invention. The fundamental form is, according to FIG. 3, formed by two-phase waveforms of the sinus-form in the frequency range of 1 to 30 Hz and with a magnetic flux density of 0.01 to 5 mT at a proportion of harmonics of approximately 1% or less. The induced electric component (E), for example, reaches approximately 3 to 9 mV/cm at a sinus waveform having a frequency (f) of 20 Hz in the radius (r) of a wound surface of 1 to 3 cm and a flux density B of 5 mT (E=π·f·r·B). This basic form of the electromagnetic field which is largely free of harmonics has a relatively low electric induction of less than 1 mV/cm which corresponds to a pH-value of less than 7. This pH-value corresponds, for example, to the acidic ichor which increasingly appears directly after the beginning of the treatment, namely on the first to the third day. At a rising pH-value of approximately 7, the growth of the connective tissue begins with increasing cell proliferation. Its stimulation is achieved at an unchanging frequency of the inducing electromagnetic field of 20 Hz by a change of the inducing electromagnetic field corresponding to the rising curve of the pH-value according to FIG. 4 by modulating the gradient of the rising edges of the sinus waveform until the pH-value of 8 characteristic for the growth phase can be measured. It is also possible to drift the trailing edge of the waveform with a larger absolute slope value. The change of the edge slope dB/dt of the inducing electromagnetic field maximally corresponds to a physiologically effective sinus frequency of 1 kHz, preferably of 200 to 500 Hz (corresponding to harmonics having a frequency of up to fifty times, preferably ten to twenty-five times the fundamental oscillation frequency of 20 Hz). The pH-value of 8 characterises the development of the autonomous granulation tissue forming the biological basis for the skin transplant. The waveform of the electromagnetic field stimulating growth is maintained until a decreasing pH-value indicates the end of the growth phase and the beginning of re-epithelialisation. In the course of the skin formation at pH-values of less than 7 or even in the range of pH 4, the electric stimulation of the tissue growth is to be minimised to the benefit of the magnetically stimulated differentiation of cells and tissue structures by returning to the temporally symmetric sinus waveform. This is substantially free of harmonics. In this way, an undifferentiated excessive growth of connective tissue such as the formation of scar keloid is avoided. The scar stimulated by the apparatus according to the invention has an unobstrusive form and achieves the elastic function of the surrounding unaffected skin.

Figure 5:
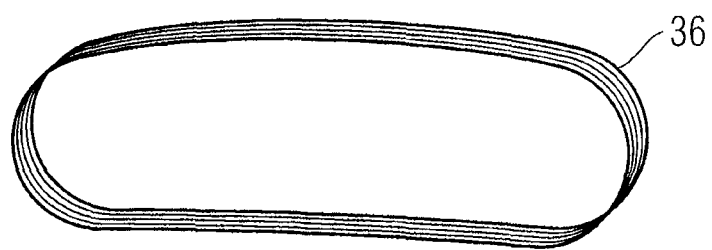
FIG. 5 shows a coil arrangement suitable for an apparatus according to the invention in a first state.
Figure 6:
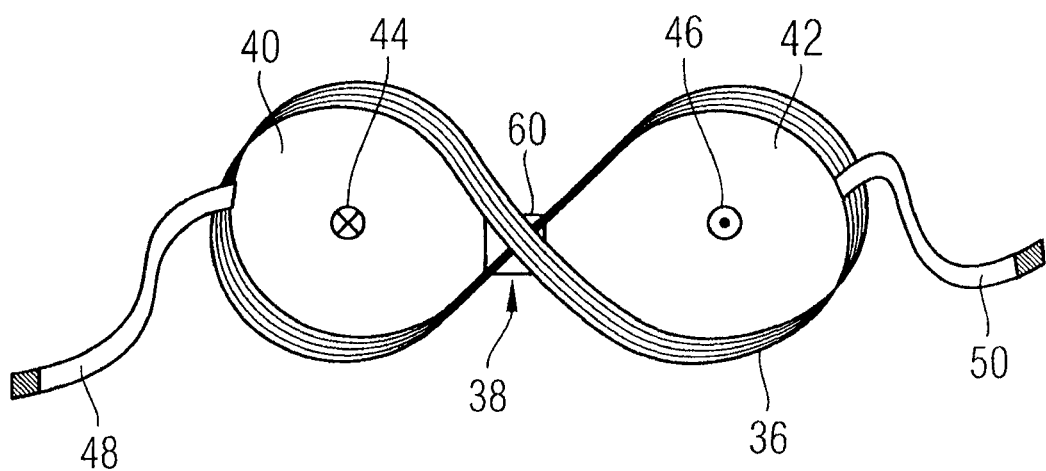
FIG. 6 shows a coil arrangement suitable for an apparatus according to the invention in a second state.
Figure 7:
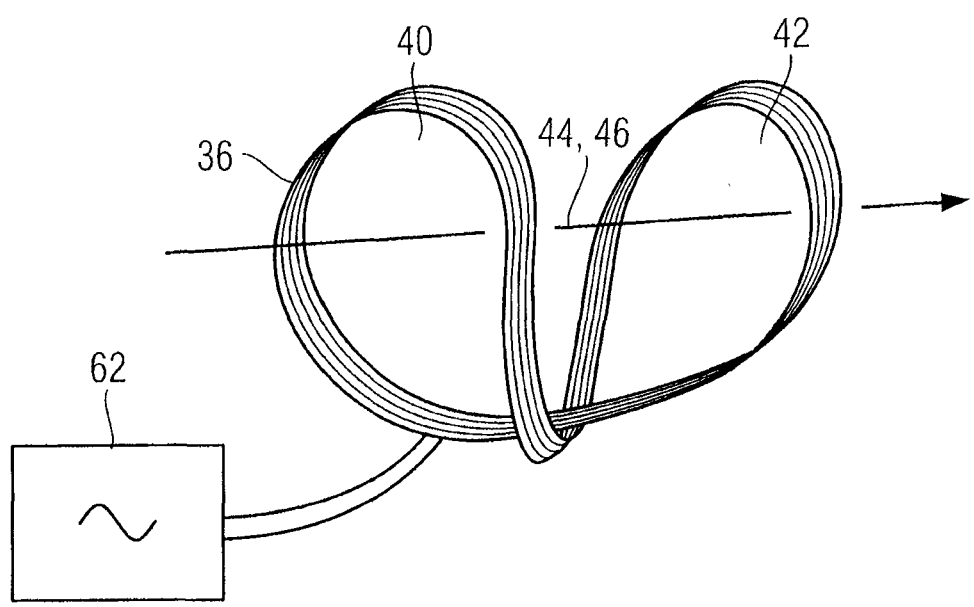
FIG. 7 shows a schematic representation for explaining the spatial alignment of a magnetic field generated by a coil arrangement according to the invention.

FIG. 5 shows a coil arrangement suitable for an apparatus according to the invention in a first state. FIG. 6 shows a coil arrangement suitable for an apparatus according to the invention in a second state. FIG. 7 shows a schematic representation for explaining the spatial alignment of a magnetic field generated by a coil arrangement according to the invention. If the flexibility of the coil arrangement 36 is used to arrange it in a figure eight shaped form, two surfaces 40, 42 and an intersection point 38 are defined. The intersection point 38 is fixed by a coupling device 60 and can preferably be shifted so that the ratio of the surfaces 40, 42 is variable. For example, an elastic belt provided with a loop-and-hook fastener or a belt buckle can serve as the coupling device 60. It is also feasible to equip the surfaces of the coil arrangement so that they form the components of a loop-and-hook fastener and can, in this way, directly adhere to each other in different positions. To facilitate adjustment, marks or scales can be provided in the variation range; the user can refer to these if he wishes to implement a specific fixation of the intersection point 38. If an alternating current flows through such a coil arrangement 36, the induced magnetic fields will have opposite directions as indicated by the vector symbols 44, 46. Owing to the flexibility of the coil arrangement 36, it can also be arranged in another shape. This is shown in connection with FIG. 1 in which a leg with a wound area 10 is shown as an example for an affected body region. The surfaces 40, 42 face each other, and the magnetic fields generated in the respective segments of the coil have the same direction. This is illustrated again in FIG. 7 in which a functional power generator 62 coupled to the coil arrangement is also shown, namely by the uniform magnetic field vector 44, 46 pervading both surfaces 40, 42. According to FIG. 1, the magnetic field pervades the affected body region largely perpendicular to the longitudinal axis of the extremity. It is also possible that the extremity runs through the surfaces defined by the loops of the figure eight shaped coil so that the magnetic field is then largley parallel to the axis of the extremity.

Figure 8:
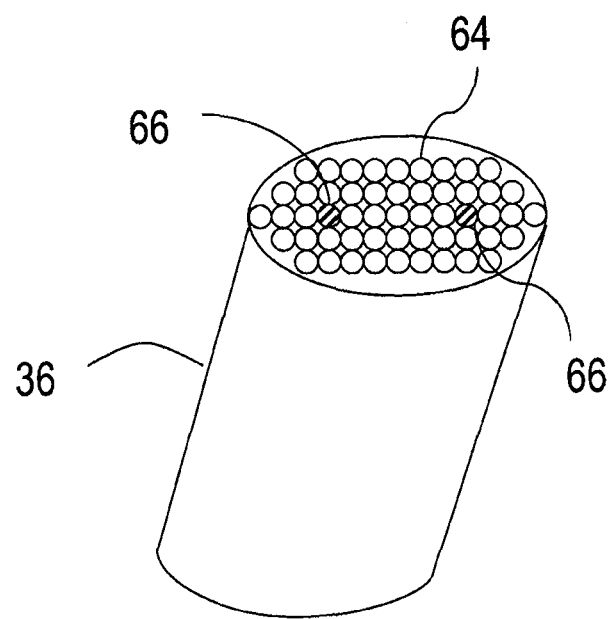
FIG. 8 shows a cut perspective partial representation of a coil arrangement having plastic features.

FIG. 8 shows a cut perspective partial representation of a coil arrangement with plastic features. The electrically conductive coil winding 64 can be seen within the coil arrangement 36. In addition, two strands 66 of a plastic material are provided in parallel to the coil winding 64 which renders the overall coil arrangement 36 plastically flexible.

Figure 9:
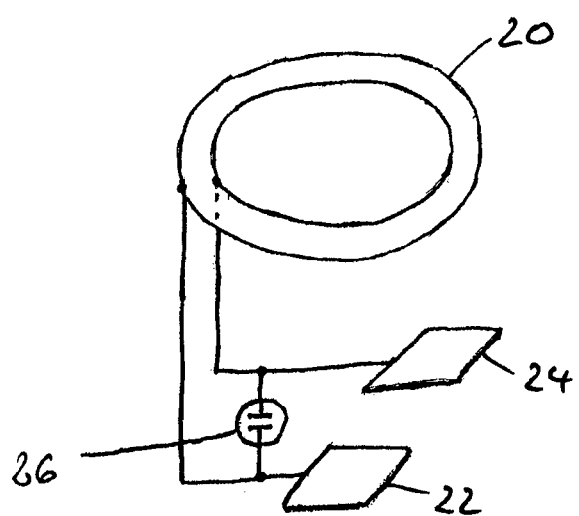
FIG. 9 an arrangement suitable for the framework of an apparatus according to the invention.

FIG. 9 shows an arrangement applicable within the framework of an apparatus according to the invention. A repeating coil 20 is shown, and the poles thereof are connected to a wound electrode 22, 24. This arrangement may be provided in addition to the apparatus discussed in connection with FIGS. 1 to 7. The electromagnetic field directly pervading the wound area also excites the repeating coil 20 which assumes the function of a secondary coil so that an electric voltage occurs between the wound electrodes 22, 24. Said wound electrodes 22, 24 can be selectively positioned in the wound area and thus support the healing process in a useful manner. To avoid voltages exceeding the tissue-compatible scale, a surge protection diode 26 is provided for limiting the voltage. Based on this arrangement, the bacterial infection of a wound can be controlled, and its antibiotic treatment will succeed. With the proportions of the EMF induction provided for stimulating wound healing, the activity of the antibiotic treatment can be increased by approximately 80%, and the inhibiting effect of the antibiotics on wound healing can be avoided. In the case of infections of chronic wounds, for example, with MRSA (Methicillin-resistant *Staphylococcus aureus*) which is one of the most dangerous germs, the magnetically induced electro-stimulation subject to pH-control and an additional application of metal electrodes in (galvanic) contact to the wound surfaces has proven indispensable. In in-vitro experiments with electrodes in the bacteria suspension, the effectivity of the antibiotic Gentamicin against *staphylococcus aureus* could be increased to 98%. In view of the increasing infection risk, particularly in surgical clinics, this discovery is of a high social and economic value. It is also possible to rectify the alternating voltage generated by the repeating coil 20 or to partly convey direct voltage characteristics to it. The wound electrode acting as an anode should then be positioned outside the wound, in particular on the healthy skin, and the wound electrode acting as the cathode should be positioned on the wound.

The features of the invention disclosed in the above description, in the drawings as well as in the claims may be important for the realisation of the invention individually as well as in any combination.

LIST OF NUMERALS 10 affected body region
12 control unit
14 input interface/reading device/receiver
16 sensor array/pH-sensor
18 transmission device/RHO transponder/transmitter
20 repeating coil
22 wound electrode
24 wound electrode
26 surge protection diode
30 leg
36 coil arrangement/magnetic coil/coil
38 intersection point
40 surface
42 surface
44 magnetic field/magnetic field vector/vector symbol
46 magnetic field/magnetic field vector/vector symbol
48 fixation means
50 fixation means
60 coupling device
62 functional power generator
64 coil winding
66 plastic strand

The invention claimed is:

1. An apparatus for stimulating a healing process comprising
   a functional power generator;
   a coil arrangement that is coupled to the functional power generator for generating an electromagnetic field in an affected external body region;
   a control unit configured to influence a voltage curve generated by the functional power generator based on signals transmitted to an input interface of the control unit;
   a sensor array configured to detect a characteristic of the affected external body region; and
   a transmission device that is coupled to the sensor array for transmitting signals characteristic of the detected characteristic of the affected external body region to the control unit, wherein
      the functional power generator is configured to generate virtually purely harmonic voltage curves having a first harmonic component and abnormally harmonic voltage curves having a second harmonic component, which is greater than the first harmonic component, based on the detected characteristics of the affected external body region.

2. The apparatus according to claim 1, wherein the sensor array comprises a pH-sensor.

3. The apparatus according to claim 1, wherein the transmission device comprises at least one electric line directly connected to the input interface of the control unit.

4. The apparatus according to claim 1, wherein the transmission device comprises at least one transmitter for a wireless communication with a receiver associated with the input interface of the control unit.

5. The apparatus according to claim 1, wherein the transmission device comprises at least one RFID transponder an information content of which is detectable by a reading device associated with the input interface of the control unit.

6. The apparatus according to claim 5, wherein the information content which is detectable by the reading device of the RFID transponder can be changed dependent on signals supplied by the sensor array.

7. The apparatus according to claim 5, wherein a plurality of RFID transponders are provided which can be activated or deactivated depending on signals supplied by the sensor array.

8. The apparatus according to claim 1, wherein the sensor array comprises an ion-sensitive field effect transistor.

9. The apparatus according to claim 1, wherein the coil arrangement comprises a coil comprising a coil winding having an intersection point and defining two surfaces owing to a figure eight shaped form, the surfaces being aligned relative to each other so that magnetic fields generated by a current flow in the coil arrangement and pervading the surfaces are substantially rectified.

10. The apparatus according to claim 9, wherein the coil arrangement is flexible so that the surfaces can be positioned on opposing sides of the affected external body region.

11. The apparatus according to claim 1, wherein the functional power generator is capable of generating a virtually purely harmonic voltage curve having a frequency of 1 to 30 Hz at a pH-value detected by the sensor array of less than 7, and of generating an abnormally harmonic voltage curve having a fundamental frequency of 1 to 30 Hz and physiologically effective harmonics with five to fifty times the fundamental frequency at a pH-value detected by the sensor array of more than 7.

12. The apparatus according to claim 1, wherein electrodes coupled to a repeating coil are provided for being positioned in or at the affected external body region.

13. The apparatus according to claim 1, wherein the generated virtually purely harmonic voltage curves alternate between voltage curves having the first harmonic component and voltage curves having the second harmonic component.

14. The apparatus according to claim 1, wherein the coil arrangement extends around a majority of an outer diameter of the affected external body region.

\* \* \* \* \*